(12) United States Patent
Baron

(10) Patent No.: US 7,691,833 B2
(45) Date of Patent: Apr. 6, 2010

(54) COMPOSITIONS AND METHODS FOR PREVENTING SPORADIC NEOPLASIA IN COLON

(75) Inventor: John A. Baron, Norwich, VT (US)

(73) Assignee: Trustees of Dartmouth College, Hanover, NH (US)

( * ) Notice: Subject to any disclaimer, the term of this patent is extended or adjusted under 35 U.S.C. 154(b) by 419 days.

(21) Appl. No.: 10/382,172

(22) Filed: Mar. 3, 2003

(65) Prior Publication Data
US 2004/0033997 A1 Feb. 19, 2004

Related U.S. Application Data

(60) Provisional application No. 60/361,251, filed on Mar. 1, 2002, provisional application No. 60/450,390, filed on Feb. 26, 2003.

(51) Int. Cl.
*A61K 31/60* (2006.01)
(52) U.S. Cl. .................................... 514/165
(58) Field of Classification Search .................. 514/165
See application file for complete search history.

(56) References Cited

U.S. PATENT DOCUMENTS

| | | | | | |
|---|---|---|---|---|---|
| 5,041,430 | A | * | 8/1991 | Addicks et al. | 514/161 |
| 5,843,929 | A | * | 12/1998 | Larson et al. | 514/182 |
| 2005/0119238 | A1 | * | 6/2005 | Baron | 514/165 |

OTHER PUBLICATIONS

Merck Index 10th edition, Windholz et al Eds. Merck & Co., Rahway NJ. 1983, abstract #863.*
Strul et al, 136CA:363133, 2000.*
Strul et al., "Non-Steroidal Anti-Inflammatory Drugs and Selective Apoptotic Anti-Neoplastic Drugs in the Prevention of Colorectal Cancer: The Role of Super Aspirins" 2000, IMAJ, 2(9), 695-702.*
Ruffin et al, Suppression of Human Colorectal Mucosal Prostaglandins: Determining the Lowest Effective Aspirin Dose, 1997, Journal of the National Cancer Institute, vol. 89, No. 15, pp. 1152-1160.*
Barnes et al, Effect of Aspirin on Prostaglandin E2 Formation and Transforming Growth Factor alpha Expression in Human Rectal Mucosa from Individuals with a History of Adenomatous Polyps of the Colon, 1999, Cancer Epidemiology, Biomarkers and Prevention, vol. 8, pp. 311-315.*
Sample et al, A Dose-Finding Study of Aspirin for Chemoprevention Utilizing Rectal Mucosal Protaglandin E2 Levels as a Biomarker, 2002, Cancer Epidemiology, Biomarkers and Prevention, vol. 11, pp. 275-279.*
Krishnana et al, Colonic Mucosal Prostaglandin E2 and Cyclooxygenase Expression Before and After Low Aspirin Doses in Subjects at High Risk or at Normal Risk for Colorectal Cancer, 2001, Cancer Epidemiology, Biomarkers and Prevention, vol. 10, pp. 447-453.*
Muir et al, Aspirin, NSAIDs and Colorectal Cancer—What do the Epidemiological Studies Show and What do They Tell Us About the Modus Operandi?, 1999, Apoptosis, vol. 4, pp. 389-396.*
E. Giovannucci, The Prevention of Colorectal Cancer by Aspirin Use, 1999, Biomed and Pharmacother, vol. 53, pp. 303-308.*
DuBois et al, Cyclooxygenase, NSAIDs, and Colorectal Cancer, 1996, J. Gastroenterol., vol. 31, pp. 898-906.*
Elder et al, Are Aspirin and Other Non-Steroidal Anti-Inflammatory Drugs Effective in the Prevention and Treatment of Colorectal Cancer?, 1996, The Lancet, vol. 348, p. 485.*
Baron et al, Could Aspirin Really Prevent Colon Cancer?, 1991, The New England Journal of Medicine, vol. 325, No. 23, pp. 1644-1646.*
Neugut et al, The Effect of Calcium and Vitamin Supplements on the Incidence and Recurrence of Colorectal Adenomatous Polyps, Cancer, 1996, vol. 78, pp. 723-728.*
Greenberg et al, Reduced Risk of Large-Bowel Adenomas Among Aspirin Users, J. Natl. Cancer Inst., 1993, vol. 85, pp. 912-916.*
Greenberg et al, Prospects for Preventing Colorectal Cancer Death, Journal of the National Cancer Institute, 1993, vol. 85, No. 15, pp. 1182-1184.*
Kune et al, Colorectal Cancer Risk, Chronic Illnesses, Operations, and Medications: Case Control Results from the Melbourne Colorectal Cancer Study, Cancer Research, 1988, vol. 48, pp. 4399-4403.*
Baron et al, Nonsteroidal Anti-Inflammatory Drugs and Cancer Prevention, Annu. Rev. Med, 2000, vol. 51, pp. 511-523.*
Sandler et al, Use of Vitamins, Minerals, and Nutritional Supplements by Participants in a Chemoprevention Trial, Cancer, 2001, vol. 91, No. 5, pp. 1040-1045.*
John A. Baron, Aspirin and Cancer, Preventive Medicine, 1995, vol. 24, pp. 121-124.*

(Continued)

*Primary Examiner*—Sreeni Padmanabhan
*Assistant Examiner*—Kendra D Carter
(74) *Attorney, Agent, or Firm*—Licata & Tyrrell P.C.

(57) ABSTRACT

Compositions and methods for preventing sporadic neoplasia of the colon are provided. The compositions provided are based on administration of acetylsalicylic acid.

1 Claim, No Drawings

OTHER PUBLICATIONS

Giardiello et al., "Treatment of Colonic and Rectal Adenomas with Sulindac in Familial Adenomatous Polyposis", New England Journal of Medicine 1993 328:1313-1316.

Giovannucci et al., "Aspirin and the Risk of Colorectal Cancer in Women", New England Journal of Medicine 1995 333(10):1593-1596.

Greenberg et al., "Reduced Risk of Large-Bowel Adenomas Among Aspirin Users", J. Natl. Cancer Inst. 1993 85:912-916.

Lamprecht and Lipkin, "Cellular Mechanisms of Calcium and Vitamin D in the Inhibition of Colorectal Carcinogenesis", Annals New York Academy of Sciences 2001 952:73-78.

Labayle et al., "Sulindac Causes Regression of Rectal Polyps in Familial Adenomatous Polyposis", Gastroenterology 1991 101:635-639.

Ladenheim et al., "Effect of Sulindac on Sporadic Colonic Polyps", Gastroenterology 1995 108:1083-1087.

Liang and Zeger, "Longitudinal data analysis using generalized linear models", Biometrika 1986 13-22.

Mayer R.J., "Tumors of the Large and Small Intestine", Harrison's Principles of Internal Medicine, Chapter 257 1424-1428.

Reddy et al., "Inhibitory effect of aspirin on azoxymethane-induced colon carcinogenesis in F344 rats", Carcinogenesis 1993 14(8):1493-1497.

Rosenberg et al., "A Hypothesis:Nonsteroidal Anti-Inflammatory Drugs Reduce the Incidence of Large-Bowel Cancer", 1998 82(12):2326-2333.

Rosenberg et al., "Nonsteroidal Antiinflammatory Drug Use and Reduced Risk of Large Bowel Carcinoma", Cancer 1998 82(12):2326-2333.

* cited by examiner

COMPOSITIONS AND METHODS FOR PREVENTING SPORADIC NEOPLASIA IN COLON

INTRODUCTION

This application claims the benefit of U.S. Provisional Application No. 60/361,251 filed Mar. 1, 2002 and U.S. Provisional Application filed Feb. 26, 2003 60/450,390.

This invention was supported in part by funds from the U.S. government (National Cancer Institute Grant No. RO1-CA59005). The U.S. government may therefore have certain rights in this invention.

BACKGROUND OF THE INVENTION

Neoplasia of the large bowel, colon or rectum is one of the most common forms of cancer, second only to lung cancer as a cause of cancer death in the United States. The etiology for most cases of large bowel cancer appears to be environmental, with much research having been focused on dietary links to cancer of the colorectum. Although as many as 25% of patients with colorectal cancer may have a family history of the disease (most evident in Familial Adenomatous Polyposis (FAP) or Hereditary Non-Polyposis Colon Cancer (HNPCC)) the majority of patients have no such family history and are said to have sporadic neoplasia. Once a tumor has been detected, treatment involves surgical removal of the tumor and often large portions of the affected colon.

Dietary alteration has been well studied as a method to reduce the risk of colon cancer. Although two of the risk factors for development of the disease were thought to be ingestion of high levels of animal fat and ingestion of a diet low in fiber, clinical trials have shown that reduction in dietary fat and increases in dietary fiber may not reduce the risk of colorectal neoplasia. Other efforts at reducing the risk of development of colon cancer have focused on intake of calcium supplements, which may inactivate bowel carcinogens through formation of insoluble soaps (Mayer (1994) In: Harrison's Principles of Internal Medicine, Chapter 257, pgs. 1424-1428) or may affect cancer risk through effects mediated by the extracellular calcium sensing receptor (Lamprecht and Lipkin (2001) *Annals New York Academy of Sciences* 952:73-87).

Aspirin (acetylsalicylic acid), an inhibitor of arachidonic acid metabolism, has been shown to inhibit the growth of colon tumors in rodents. Studies have also suggested that aspirin use is protective against carcinogenesis in the large bowel (Greenberg, et al. (1993) *J. Natl. Cancer Inst.* 85:912-916; Giovannucci, et al. (1995) *New Engl. J. Med.* 333:609-14; Thun, et al. (1991) *New Engl. J. Med.* 325:1593-1596). Several studies have also shown that sulindac, a non-steroidal anti-inflammatory drug, may have use as a preventative treatment for hereditary polyposis of the colon and rectum (Labayle, et al. (1991) *Gastroenterology* 101:635-639; Ladenheim, et al. (1995) *Gastroenterology* 108:1083-1087; Giardiello, et al. (1993) *New Engl. J. Med.* 328:1313-1316). However, there remains a need for substances that can prevent colon cancer in humans.

SUMMARY OF THE INVENTION

An object of the present invention is a composition that can prevent sporadic neoplasia of the large bowel that comprises an effective amount of acetylsalicylic acid and a pharmaceutically acceptable vehicle.

Another object of the present invention is a method for preventing sporadic neoplasia of the large bowel in a patient that comprises administering to a patient an effective amount of an acetylsalicylic acid composition so that sporadic neoplasia of the large bowel is prevented.

These and other aspects of the present invention are set forth in more detail in the following description of the invention.

DETAILED DESCRIPTION OF THE INVENTION

Although observational (epidemiological) studies have suggested that aspirin, known by the chemical name of acetylsalicylic acid, is protective against carcinogenesis in the large bowel, there has previously been no experimental evidence in humans that would definitively link use of acetylsalicylic acid as a treatment to prevent cancer in humans. In order to provide such definitive evidence of a therapeutic effect in humans, clinical, randomized trials are routinely performed. It has now been found that in a randomized, double-blind, placebo-controlled study in humans that acetylsalicylic acid protects against the recurrence of large bowel neoplasia in patients with sporadic (non-hereditary) colorectal neoplasia (adenomas). A 19 percent reduction in risk of one or more adenomas was found for 81 mg aspirin, a non-significant 4 percent reduction with 325 mg aspirin, and a non-significant 12 percent reduction for both aspirin groups combined. More than a 40% reduction in risk for advanced lesions with 81 mg aspirin was found. Therefore, acetylsalicylic acid (aspirin) is an effective treatment for prevention of colon cancer in humans.

A multi-center, randomized, double-blind, placebo-controlled study was performed that examined the effects of aspirin alone as well as folate treatment combined with aspirin on the occurrence of large bowel adenomas. The study has a 3-by-2 factorial design, investigating aspirin (placebo, 81 mg/day, or 325 mg/day) and folic acid (placebo or 1 mg/day). Patients were recruited at nine centers in North America. Eligible subjects had at least one of the following: (1) one or more histologically confirmed large-bowel adenomas removed within 3 months prior to recruitment, (2) one or more histologically confirmed large-bowel adenomas removed within 16 months before recruitment and a lifetime history of 2 or more confirmed large-bowel adenomas, or (3) a histologically confirmed large-bowel adenoma at least 1 cm in diameter removed within 16 months before recruitment. Each subject was also required to have had a complete colonoscopy within 3 months of recruitment, with no known large bowel polyps remaining. Eligible subjects were between 21 and 80 years old, in good health, and with anticipated colonoscopic follow-up three years after the qualifying examination. Exclusion criteria included a history of a familial colorectal cancer syndrome, invasive large-bowel cancer, malabsorption syndromes, any condition potentially worsened by supplemental aspirin or folic acid, or any condition commonly treated with aspirin, non-steroidal anti-inflammatory drugs (NSAIDs), or folate (e.g., recurrent arthritis, atherosclerotic vascular disease, folic acid deficiency).

Of the 1,409 eligible subjects that were considered for the study, 1,121 were randomized to aspirin. 288 subjects were not randomized due to death, bleeding or other apparent toxicity, an inability to avoid study agents, ineligibility for reasons related to the folate component of the study (e.g., anemia), intercurrent illness, non-compliance, and declining to continue. In the case of the folate aspect of the study, only 1,121 patients were randomized because 100 subjects had been entered into the aspirin study before the folate arms were initiated. The numbers of randomized patients ranged from 97 to 157 across clinical centers. There were no substantial differences between baseline characteristics treatment groups in terms of demographic, lifestyle or clinical characteristics (Table 1).

TABLE 1

|  | Placebo N = 372 | 81 mg Aspirin N = 377 | 325 mg Aspirin N = 372 |
|---|---|---|---|
| Mean Age, years (SD) | 57.4 (9.9) | 57.3 (9.9) | 57.7 (9.1) |
| Male N, (percent) | 233 (62.6) | 244 (64.7) | 235 (63.2) |
| Race |  |  |  |
| White, not Hispanic, N (percent) | 307 (82.5) | 329 (87.3) | 322 (86.6) |
| Black, not Hispanic, N (percent) | 27 (7.3) | 22 (5.8) | 19 (5.1) |
| Hispanic, N (percent) | 27 (7.3) | 16 (4.2) | 18 (4.8) |
| Asian/Pacific/Other, N (percent) | 11 (3.0) | 10 (2.6) | 13 (3.5) |
| Mean body mass index, $kg/m^2$ (SD) | 27.3 (4.4) | 27.3 (4.4) | 27.7 (4.7) |
| Current cigarette smoker, N (percent) | 53 (14.3) | 59 (15.7) | 55 (15.9) |
| Colorectal cancer in $1^{st}$ degree relative, N (percent) | 105 (28.2) | 111 (29.4) | 125 (33.6) |
| Mean number of reported lifetime adenomas before randomization, (SD) | 2.4 (2.2) | 2.2 (2.0) | 2.4 (2.4) |
| Qualified for study with 1 lifetime adenoma, N (percent) | 166 (44.9) | 177 (47.1) | 171 (46.1) |
| Qualified for study with adenoma ≧ 1 cm, N (percent) | 124 (33.3) | 108 (28.6) | 127 (34.1) |
| Mean number of adenomas on examinations qualifying for study entry (SD) | 1.6 (1.0) | 1.6 (1.0) | 1.6 (1.0) |
| Mean estimated diameter of largest qualifying adenoma, cm (SD) | 0.7 (0.5) | 0.7 (0.5) | 0.7 (0.5) |
| Mean baseline dietary calcium intake, mg (SD) | 780 (436) | 737 (366) | 759 (463) |
| Mean baseline dietary folate intake, μg (SD) | 328 (161) | 313 (158) | 319 (151) |

Data on smoking status were missing for five patients, data on body-mass index, reported adenomas before randomization, and qualification for the study with history of 1 adenoma were missing for four patients, and data on dietary information were missing for 55 patients.

1,084 randomized subjects (96.7 percent) underwent a follow-up examination (Table 2), and in 1,049 (96.8 percent), the entire large-bowel mucosa was visualized.

TABLE 2

|  | Placebo N = 372 | 81 mg Aspirin N = 377 | 325 mg Aspirin N = 372 |
|---|---|---|---|
|  | Number of subjects (percent) | | |
| Died, N (percent) | 3 (0.8) | 3 (0.8) | 4 (1.1) |
| No follow-up examination, N (percent) | 5 (1.3) | 7 (1.9) | 13 (3.5) |
| Follow-up examination only in $1^{st\ year\ after}$ randomization, N (percent) | 1 (0.3) | 1 (0.3) | 0 (0.0) |
| Had follow-up examination at least 1 year after randomization, N (percent) | | | |

TABLE 2-continued

|  | Placebo N = 372 | 81 mg Aspirin N = 377 | 325 mg Aspirin N = 372 |
|---|---|---|---|
|  | Number of subjects (percent) | | |
| Total number evaluated | 363 | 366 | 355 |
| In protocol window | 318 (87.6) | 332 (90.7) | 309 (87.0) |
| Early follow-up exam | 10 (2.8) | 10 (2.7) | 9 (2.5) |
| Late follow-up exam | 35 (9.6) | 24 (6.6) | 37 (10.4) |
| Entire large bowel mucosa well visualized | 349 (96.1) | 357 (97.5) | 343 (96.6) |
| Had interim* endoscopy N (percent) | 12 (3.3) | 12 (3.3) | 18 (5.1) |
| Mean follow-up interval, months (SD) | 32.9 (4.2) | 32.5 (3.4) | 32.8 (3.7) |

*exam after randomization prior to surveillance exam.

Study coordinators at each center maintained contact with the subjects on a regular basis; interval questionnaires regarding possible side effects and medical events were completed every four months by each subject. Reported compliance with the study protocol was excellent, and was similar across treatment groups (Table 3).

TABLE 3

|  | Placebo (N = 363) | 81 mg aspirin (N = 366) | 325 mg aspirin (N = 355) |
|---|---|---|---|
|  | Number of subjects/total number (percent) | | |
| Adherence to Study Tablets | | | |
| Year 1 | | | |
| 6–7 days per week | 333/358 (93.0) | 338/357 (94.7) | 332/351 (94.6) |
| 3–5 days per week | 19/358 (5.3) | 9/357 (2.5) | 11/351 (3.1) |
| <3 days per week | 6/358 (1.7) | 10/357 (2.8) | 8/351 (2.3) |
| Year 2 | | | |
| 6–7 days per week | 315/353 (89.2) | 324/358 (90.5) | 317/349 (90.8) |
| 3–5 days per week | 18/353 (5.1) | 17/358 (4.7) | 16/349 (4.6) |
| <3 days per week | 20/353 (5.7) | 17/358 (4.7) | 16/349 (4.6) |
| Year preceding follow-up exam | | | |
| 6–7 days per week | 298/342 (87.1) | 317/353 (89.8) | 301/342 (88.0) |
| 3–5 days per week | 15/342 (4.4) | 20/353 (5.7) | 20/342 (5.8) |
| <3 days per week | 29/342 (8.5) | 16/353 (4.5) | 21/342 (6.1) |
| Non-Protocol Non-Steroidal Anti-Inflammatory Drug Use | | | |
| Year 1 | | | |
| none | 259/359 (72.1) | 269/361 (74.5) | 262/352 (74.4) |
| 1–4 days/month | 86/359 (23.9) | 77/361 (21.3) | 78/352 (22.2) |
| >4 days/month | 14/359 (3.9) | 15/361 (4.2) | 12/352 (3.4) |
| Year 2 | | | |
| none | 246/356 (69.1) | 250/362 (69.1) | 251/352 (71.3) |
| 1–4 days/month | 87/356 (24.4) | 87/362 (24.0) | 75/352 (21.3) |
| >4 days/month | 23/356 (6.5) | 25/362 (6.9) | 26/352 (7.4) |
| Year preceding follow-up exam | | | |
| none | 227/351 (64.7) | 248/359 (69.1) | 226/346 (65.3) |
| 1 day/month | 91/351 (25.9) | 79/359 (22.0) | 87/346 (25.1) |
| >4 days/month | 33/351 (9.4) | 32/359 (8.9) | 33/346 (9.5) |

Only subjects who underwent a follow-up examination at least one year after randomization are included in this analysis. Table entries are based on the numbers of patients who responded to interval questionnaires regarding compliance.

During the first year of participation, 94.1 percent of subjects reported taking virtually all study tablets, and another 3.7 percent reported taking at least half. Even in the year before the final follow-up colonoscopy, 88.3 percent of subjects reported taking 90 percent or more of the study tablets and another 5.3 percent at least half. Subjects were also successful in avoiding non-protocol use of aspirin and other non-steroidal anti-inflammatory drugs (NSAIDs). During the first year, 73.7 percent of subjects reported no NSAID use; only 3.8 percent reported taking NSAIDs on more than four days a month on average. In the year before the follow-up examination, these proportions were 66.4 percent and 9.3 percent, respectively.

Among the 1,084 patients with follow-up examinations, a total of 1,812 polyps were seen in 670 subjects. Fifty-eight of 664 polyps (8.7 percent) in placebo subjects were lost or not removed, as were 47 of 497 (9.5 percent) in the 81 mg aspirin group, and 41 of 651 (6.3 percent) in the 325 mg aspirin group. At least one colorectal adenoma was diagnosed in 47.1 percent of subjects assigned placebo, 38.3 percent of subjects randomized to 81 mg/day aspirin, and 45.1 percent among those taking 325 mg/day aspirin (P=0.04) (Table 4).

TABLE 4

| | N with adenoma/N followed (percent) | Relative Crude Risk (95% CI) | P value# | Adjusted Relative Risk (95% CI)* | P value# |
|---|---|---|---|---|---|
| Any Adenoma | | | | | |
| Placebo | 171/363 (47.1%) | 1.00 (reference) | | 1.00 (reference) | |
| Aspirin | 300/721 (41.6%) | 0.88 (0.77–1.02) | | 0.89 (0.77–1.03) | |
| 81 mg Aspirin | 140/366 (38.3%) | 0.81 (0.69–0.96) | | 0.83 (0.70–0.98) | |
| 325 mg Aspirin | 160/355 (45.1%) | 0.96 (0.81–1.13) | 0.06 | 0.95 (0.80–1.12) | 0.14 |
| Advanced Lesion | | | | | |
| Placebo | 47/363 (12.9%) | 1.00 (reference) | | 1.00 (reference) | |
| Aspirin | 66/721 (9.2%) | 0.71 (0.50–1.00) | | 0.70 (0.49–0.99) | |
| 81 mg Aspirin | 28/366 (7.7%) | 0.59 (0.38–0.92) | | 0.58 (0.37–0.90) | |
| 325 mg Aspirin | 38/355 (10.7%) | 0.83 (0.55–1.23) | 0.15 | 0.83 (0.55–1.23) | 0.13 |
| Tubular Adenoma** | | | | | |
| Placebo | 143/363 (39.4%) | 1.00 (reference) | | 1.00 (reference) | |
| Aspirin | 262/721 (36.3%) | 0.92 (0.79–1.08) | | 0.93 (0.79–1.10) | |
| 81 mg Aspirin | 121/366 (33.1%) | 0.84 (0.69–1.02) | | 0.87 (0.72–1.05) | |
| 325 mg Aspirin | 141/355 (39.7%) | 1.01 (0.84–1.21) | 0.06 | 1.00 (0.83–1.20) | 0.16 |

CI denotes confidence interval.
P-values for difference between risk ratios for 81 mg aspirin and 325 mg aspirin.
*Risk ratios have been adjusted for age, sex, clinical center, length of follow-up and baseline number of lifetime adenoma.

The crude relative risk (versus placebo) for 81 mg/day of aspirin was 0.81 (95 percent confidence interval: 0.69 to 0.96) and for 325 mg/day, 0.96 (95 percent confidence interval: 0.81 to 1.13) (P for difference=0.06). The unadjusted risk ratio for the two aspirin groups combined was 0.88 (95 percent confidence interval: 0.77 to 1.02). Multivariate risk ratios were similar.

Findings varied according to type of lesion. For advanced lesions, the unadjusted risk ratios were 0.59 (95 percent confidence interval: 0.38 to 0.92) for 81 mg aspirin, and 0.83 (95 percent confidence interval: 0.55 to 1.23) for those randomized to 325 mg (P for difference of relative risks=0.15). Colorectal cancer was diagnosed in one subject in the placebo group, two in the low-dose aspirin group, and three in the higher-dose aspirin group (p=0.71). Findings were similar for adenomas in the right and left colorectum; restriction of the analysis to adenomas detected only during planned surveillance colonoscopies yielded results virtually identical to those above.

The reduced risk of advanced lesions with lower-dose aspirin was more apparent among females than among males (P for interaction=0.02) and among subjects younger than the median age (57 years old at randomization; P for interaction=0.06). The adjusted risk ratio for the detection of at least one advanced adenoma for 81 mg aspirin was 0.18 (95 percent confidence interval: 0.06 to 0.60) among women and 0.37 (95 percent confidence interval: 0.19 to 0.73) among younger subjects.

Few serious medical events were observed (Table 5).

TABLE 5

| | Placebo (N = 372) | 81 mg aspirin (N = 377) | 325 mg aspirin (N = 372) | P value‡ |
|---|---|---|---|---|
| | | no of subjects | | |
| Deaths | 3 | 3 | 4 | 0.93 |
| Hospitalization | 44 | 61 | 57 | 0.20 |
| Non-Colorectal Cancer | 6 | 14 | 9 | 0.21 |
| Colorectal Cancer | 1 | 2 | 3 | 0.71 |
| Myocardial Infarction | 1 | 2 | 4 | 0.42 |
| Coronary Revascularization | 4 | 3 | 5 | 0.76 |
| Stroke | 0 | 2 | 5 | 0.06 |
| Serious Bleeding* | | | | |
| Gastrointestinal | 3 | 2 | 4 | 0.65 |
| Genitourinary | 2 | 6 | 2 | 0.24 |

‡P values are for the differences among the three groups.
*Serious bleeding was defined as bleeding leading to hospitalization or surgical intervention.

Risks of death and serious bleeding were similar across treatment groups. Hospitalization, cancer and myocardial infarction occurred somewhat more frequently in the aspirin groups than in placebo, but the differences were clearly compatible with chance. Seven patients were diagnosed with a stroke (all non-fatal); each had been randomized to aspirin (P for heterogeneity=0.06). One stroke (in the 81 mg aspirin group) was judged to be hemorrhagic after review of the medical records.

The data provided herein show that the incidence of adenomas was significantly lower among patients randomized to the aspirin groups. Further, these data demonstrate that aspirin has a protective effect in the large bowel, preventing the reoccurrence of neoplasia in patients with sporadic (non-hereditary) colon cancer.

Therefore, the present invention is a composition for the prevention of colon cancer in humans. The composition, acetylsalicylic acid, or aspirin, was administered daily, as an oral tablet, to patients in this clinical study. The fact that this study was a randomized, double-blind, placebo-controlled study provides significant scientific weight to the results and demonstrates for the first time that the aspirin had a therapeutic effect. Therefore, the composition of the present invention in one embodiment would be an orally administered effective amount of acetylsalicylic acid. In the context of the present invention, an effective amount of the composition of the present invention is a dose of acetylsalicylic acid of between 81 and 325 mg. In a preferred embodiment, the dose of acetylsalicylic acid would be 81 mg per day. One of skill would understand that the dose of the composition of the present invention could be altered depending on the patient population treated. In addition, the composition of the present invention can be administered in forms other than tablet form that would include, but not be limited to, geltabs, time-release capsules, oral suspensions, suppositories, topical creams or gels. Each of these formulations would be chosen based on the knowledge of one of skill in the art based on the type of treatment regimen designed for the patient to be treated.

The present invention is also a method of preventing sporadic neoplasia of the large bowel in a patient. The method involves administering to the patient at risk or suspected of being at risk of developing sporadic neoplasia an effective amount of acetylsalicylic acid in a pharmaceutically acceptable vehicle so that sporadic neoplasia of the large bowel is prevented. One of skill would understand that in this method the pharmaceutically acceptable vehicle and the effective amount of acetylsalicylic acid would be chosen based on the patient population to be treated. Pharmaceutically acceptable vehicles, for example, are described in Remington's Pharmaceutical Sciences (16th ed., Osol, A. ed., Mack Easton Pa. (1980)). Examples of pharmaceutically acceptable vehicles include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

The invention is described in greater detail by the following non-limiting examples.

EXAMPLE 1

Follow-Up

Subjects were regularly counseled regarding avoidance of aspirin and other NSATDs. Lists of products containing aspirin, ibuprofen, or naproxen were provided, and acetaminophen was distributed for treatment of minor febrile illnesses and pain. Every four months, subjects received questionnaires regarding adherence to study treatment; use of medications, over-the-counter drugs and nutritional supplements; and occurrence of symptoms, illnesses, and hospitalizations. Lists of brand and chemical names of all available NSAIDs were included in the questionnaires, and subjects were asked if they had taken any of the listed drugs.

By protocol, subjects were to have a complete surveillance colonoscopy 34-40 months after the qualifying examination. At each colonoscopy, the endoscopist recorded the estimated size and location of all polyps and mucosal lesions suspicious for neoplasia as per usual clinical practice. Each lesion was removed and examined histologically at the clinical center and by the study pathologist. Polyps were classified as neoplastic (adenomatous) or non-neoplastic (e.g., hyperplastic) by the study pathologist.

The primary study outcome was the proportion of subjects with one or more colorectal adenomas detected during the period from one year after randomization through the anticipated surveillance follow-up. If a surveillance colonoscopy was not performed during the protocol time window, the last examination at least one year after randomization was taken as the follow-up exam. Pre-specified secondary outcomes were the numbers of large-bowel adenomas and "advanced lesions": tubulovillous adenomas (25 to 75 percent villous features), villous adenomas (>75 percent villous), large adenomas (~1 cm), severe dysplasia, or invasive cancer. Separate analyses were also conducted for lesions in the left colorectum (descending colon, sigmoid colon, and rectum) and right colorectum (the remainder of the bowel).

EXAMPLE 2

Statistical Analysis

The statistical analysis compared the aspirin treatment groups irrespective of folic acid treatment. Subjects who underwent a follow-up endoscopy at least one year following randomization were included in the analyses. The predefined primary statistical analysis was a 2 degree-of-freedom chi-squared test for a contingency table comparing treatment groups regarding risk of one or more new adenomas. Crude risk ratios and 95 percent confidence intervals were used to compare treatment groups to placebo. Adjusted risk ratios were obtained from log-linear models with age, gender, clinical center, number of lifetime adenomas, and duration of follow-up as covariates. Among subjects in the full factorial trial, a blinded analysis with further adjustment for folate treatment assignment yielded results similar to those presented. Possible modification of treatment effects by baseline characteristics was assessed using interaction terms in the log-linear model. Counts of other clinical endpoints were compared using Fisher's exact test. To compare the effect of aspirin on different types of polyps, a logistic regression model was used with generalized estimating equations (Liang and Zeger *Biometrika* 1986:13-22) to account for the clustering of multiple endpoints within patients. Poisson regression was used to estimate ratios of numbers of recurrent adenomas by treatment group; these results were similar to those in the risk analysis. Two-sided P-values <0.05 were considered statistically significant.

What is claimed is:

1. method for decreasing the risk of developing a sporadic neoplasia of the large bowel in a patient comprising administering to a patient at risk of developing a sporadic neoplasia of the large bowel an effective amount of acetylsalicylic acid and a pharmaceutically acceptable vehicle daily for at least one year, wherein the patient is an individual that had at least one confirmed large-bowel adenoma, and wherein the effective amount of acetylsalicylic acid is 81 mg of acetylsalicylic acid so that the risk of developing a sporadic neoplasia of the large bowel is decreased.

* * * * *